United States Patent
Waynick

(10) Patent No.: US 7,018,434 B2
(45) Date of Patent: *Mar. 28, 2006

(54) REMOVAL OF DRAG REDUCER ADDITIVE FROM FUEL BY TREATMENT WITH SELECTED ACTIVATED CARBONS AND GRAPHITES

(75) Inventor: John Andrew Waynick, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 190 days.

This patent is subject to a terminal disclaimer.

(21) Appl. No.: 10/453,803

(22) Filed: Jun. 3, 2003

(65) Prior Publication Data

US 2004/0015034 A1    Jan. 22, 2004

Related U.S. Application Data

(63) Continuation-in-part of application No. 10/124,974, filed on Apr. 18, 2002, now Pat. No. 6,599,337.

(51) Int. Cl.
*C10L 1/00*    (2006.01)

(52) U.S. Cl. .......................... 44/457; 44/459; 44/903; 436/60; 210/728; 585/820; 585/823

(58) Field of Classification Search ................ 44/903, 44/457, 459; 436/60; 210/728; 585/820, 585/823
See application file for complete search history.

(56) References Cited

U.S. PATENT DOCUMENTS

| | | | |
|---|---|---|---|
| 1,198,039 A | 9/1916 | Krause | |
| 2,546,903 A | 3/1951 | Morrell | |
| 2,744,938 A | 5/1956 | Urban, Jr. | |
| 2,762,852 A | 9/1956 | Litton | |
| 3,366,582 A | 1/1968 | Adams et al. | |
| 3,977,969 A | 8/1976 | Zall | |
| 4,451,377 A | 5/1984 | Luxemburg | |
| 4,502,957 A | 3/1985 | Jehle et al. | |
| 4,508,851 A | 4/1985 | Izumi et al. | |
| 4,527,581 A | 7/1985 | Motier | |
| 4,599,117 A | 7/1986 | Luxemburg | |
| 4,720,397 A * | 1/1988 | O'Mara et al. | 427/180 |
| 4,747,855 A | 5/1988 | Hirai et al. | |
| 4,758,354 A | 7/1988 | O'Mara et al. | |
| 4,837,249 A | 6/1989 | O'Mara | |
| 5,165,440 A | 11/1992 | Johnston | |
| 5,225,081 A | 7/1993 | Brownawell | |
| 5,244,937 A | 9/1993 | Lee et al. | |
| 5,376,697 A | 12/1994 | Johnston et al. | |
| 5,504,132 A | 4/1996 | Smith et al. | |
| 5,539,044 A | 7/1996 | Dindi et al. | |
| 5,733,953 A | 3/1998 | Fairchild et al. | |
| 5,736,053 A | 4/1998 | Ikushima et al. | |
| 5,788,865 A | 8/1998 | Smirnov et al. | |
| 5,833,862 A | 11/1998 | Holland | |
| 5,884,777 A | 3/1999 | Pan et al. | |
| 5,888,402 A | 3/1999 | Hommeltoft et al. | |
| 5,891,324 A | 4/1999 | Ohtsuka | |
| 5,893,398 A | 4/1999 | Garrett, Jr. | |
| 5,900,153 A | 5/1999 | Sanford | |
| 6,024,880 A | 2/2000 | Ciora, Jr. et al. | |
| 6,027,653 A | 2/2000 | Holland | |
| 6,042,722 A | 3/2000 | Lenz | |
| 6,056,805 A | 5/2000 | Litwin et al. | |
| 6,082,392 A | 7/2000 | Watkins, Jr. | |
| 6,103,127 A | 8/2000 | Pourfarzaneh | |
| 6,599,337 B1 | 7/2003 | Waynick | |
| 2003/0019149 A1 | 1/2003 | Waynick | |

FOREIGN PATENT DOCUMENTS

GB    1236066    6/1971

OTHER PUBLICATIONS

Natalie Marchildon, et al. The AA Graphite Deposit, Bella Coola Area, British Columbia: Exploration Implications For The Coast Plutonic Complex. (92M/15) Geological Fieldwork 1992, Paper 1993-1 p. 389-397. http://www.em.gov.bc.ca/DL/GSBPubs/GeoFldWk/1992/389-398-marchildon.pdf.

Edward Matulevicius. Fuel Technology Associates. Effect of Pipeline Drag Reducer Additive on Coalescence & Filtration in Aviation Fuels. A Plan for Determining the Effect of Fully Sheard pipeline Drag Reducer Additives on Filter/Separators and Monitors. Apr. 9, 2001 http://www.crcao.com/aviation/Presentation%202001CRC%20Final%20PDR%20Plan.pdf.

* cited by examiner

*Primary Examiner*—Cephia D. Toomer
(74) *Attorney, Agent, or Firm*—Paula D. Morris; Morris & Amatong, P.C.

(57) ABSTRACT

The application relates to a method for selecting drag reducer additive (DRA) effectively removable by activated carbons and graphites to be used in fuel. The appliction also relates to effective activated carbons and graphites for removing DRA from fuel, and to a method of using effective activated carbons and graphites to remove DRA from fuel.

137 Claims, 5 Drawing Sheets

REMOVAL OF DRAG REDUCER ADDITIVE FROM FUEL BY TREATMENT WITH SELECTED ACTIVATED CARBONS AND GRAPHITES

CROSS-REFERENCE TO RELATED APPLICATIONS

This application is a continuation-in-part application of U.S. patent application Ser. No. 10/124,974, filed on Apr. 18, 2002 now U.S. Pat. No. 6,599,377.

FIELD OF THE INVENTION

The application relates to a method for selecting drag reducer additive (DRA) effectively removable by activated carbon to be used in fuel. The application also relates effective activated carbons and graphites for removing DRA from fuel, and to a method of using effective activated carbon and graphites to remove DRA from fuel.

BACKGROUND

In order to move fluid through pipelines, into or out of wells, or through equipment, energy must be applied to the fluid. The energy moves the fluid, but is lost in the form of friction. This frictional pressure drop, or drag, restricts the fluid flow, limiting throughput and requiring greater amounts of energy for pumping.

Materials can be added to flowing fluids in order to reduce the energy lost due to friction, or drag, thus permitting the movement of more fluid at the same differential pressure. The resulting reduction in frictional pressure drop improves pumping efficiency, lowers energy costs, and increases profitability. Materials for reducing drag in flowing fluids are generally known by the generic names "flow improver" or "drag reducer additive" (sometimes referred to as "DRA").

Unfortunately, whether in the virgin form or in the sheared or partially sheared form, and despite the fact that it is intentionally added to certain fuels, drag reducer additive nonetheless is a "contaminant" in liquid hydrocarbon fuels, and has the potential to cause a number of problems. For example, the presence of drag reducer additive in motor gasoline, even in the sheared form, has caused increased intake valve deposits, plugging of fuel filters, and increased combustion chamber deposits. In diesel fuels, drag reducer additive may cause plugging of fuel filters and strainers and increased fuel injector deposits. Drag reducer additive is prohibited in aviation turbine fuels, although it has been observed as a contaminant due to accidental addition or other non-intentional means. The presence of drag reducer additive in aviation turbine fuel may result in downgrading of the entire batch to non-aviation kerosene or diesel fuel, both of which generally have less market value.

Viable methods of detecting and quantifying drag reducer additive in liquid hydrocarbon fuels commonly employ gel permeation chromatography, which is time consuming and expensive. Because of this, contaminated liquid hydrocarbon fuels often are used, despite the potential problems if drag reducer additive is present. Contaminated aviation turbine fuels may be diverted to other uses or returned to a refinery for reprocessing, either of which results in additional expense. Simple and inexpensive methods and materials are needed for removing drag reducer additive from liquid hydrocarbon fuels.

SUMMARY

The application provides a method for removing drag reducer additive from a liquid hydrocarbon fuel. The method comprises providing a contaminated liquid hydrocarbon fuel comprising a concentration of a drag reducer additive, and contacting the contaminated liquid hydrocarbon fuel with a quantity of one or more of an activated carbon or a graphite effective to substantially reduce said concentration of drag reducer additive, thereby producing a clean liquid hydrocarbon fuel.

DETAILED DESCRIPTION

Figure 1:
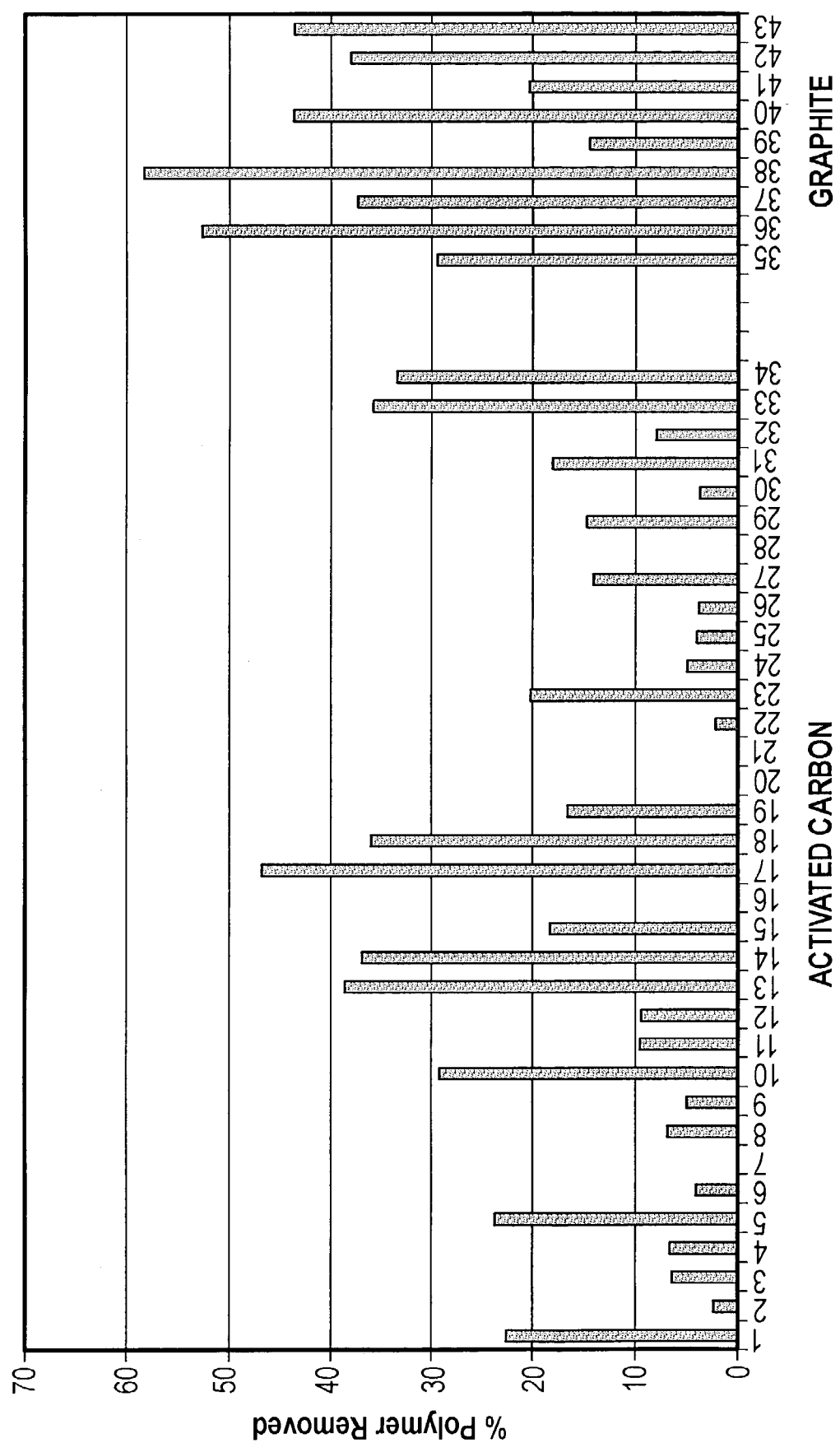
FIG. 1 is a graph of % Polymer Removed vs. Carbon (activated carbons and graphites) used to remove unsheared FLO® XS polymer from jet fuel using the Grad Add/Stir method (described in detail below).

The application provides methods for removing drag reducer additive (DRA) from liquid hydrocarbon fuels, preferably motor gasoline or jet fuel, most preferably jet fuel, using selected activated carbons or graphites. As used herein, the word "contaminated" refers to the presence of DRA in the fuel, due to either intentional addition or unintentional addition.

"Liquid Hydrocarbon Fuel"

By "liquid hydrocarbon fuel" is meant any hydrocarbon that is liquid under conditions of transport and/or storage. Suitable liquid hydrocarbon fuels include, but are not necessarily limited to those having a boiling range of from about 150° F. to about 750° F., which may be used as a fuel. In one embodiment, the liquid hydrocarbon fuel is selected from the group consisting of liquefied natural gas (LNG), liquefied petroleum gas (LPG), motor gasoline, aviation gasoline, distillate fuels such as diesel fuel and home heating oil, kerosene, jet fuel, No. 2 oil, residual fuel, No. 6 fuel, or bunker fuel. In a preferred embodiment, the liquid hydrocarbon fuel is selected from the group consisting of diesel fuel, jet fuel, aviation gasoline, and motor gasoline. In a more preferred embodiment, the liquid hydrocarbon fuel is jet fuel, at least in part due to the stringent requirements applicable to jet fuel and drag reducer additive. The phrase "jet fuel" refers to both commercial jet fuel (Jet A, Jet A-1, and JET B) and military jet fuel, such as JP-4, JP-5, JP-8 and the like.

"Drag Reducer Additive"

The term "drag reducer additive" (i.e. DRA) is defined to mean polyolefin polymers comprising polyolefin moieties which are introduced into petroleum liquids for the purpose of reducing fluid flow drag. The drag reducer additive may comprise other components besides the polyolefin moieties. Examples of such components include, but are not necessarily limited to surfactant, catalyst residue, other additives, and other byproducts from the production of the polymer. The polymer itself may contain other non-olefin monomer units as well.

In a preferred embodiment, the drag reducer additive includes, but is not necessarily limited to, non-polar long-chain polyolefin polymers, generally referred to as "polyalphaolefins," having a "peak" molecular weight sufficiently high to allow the polymers to reduce fluid flow drag. Suitable polyalphaolefins are believed to have a molecular weight of about 1 million Daltons or more, more preferably about 10 million Daltons or more, most preferably about 25 million Daltons or more. The "peak" molecular weight refers to the peak that typically is measured as the drag reducer is eluted and detected during gel permeation chromatography.

Suitable polyalphaolefins comprise polymerized linear alpha olefin (LAO) monomers having from about 2 to about 40 carbon atoms, preferably from about 2 to about 30 carbon atoms, more preferably from about 4 to about 20 carbon atoms, most preferably from about 6 to about 12 carbon atoms. An especially preferred embodiment for a DRA which is effectively removable by the activated carbons and/or graphites described herein comprises at least two different LAO's, preferably having from about 6 to about 12 carbon atoms, the number of carbon atoms of the "at least two different LAO's" differing by 6.

Polyalphaolefins having relatively high molecular weights are required to impart good drag reduction. Suitable polyalpha olefins "are made by a variety of processes, including but not necessarily limited to solution polymerization and bulk polymerization. Bulk polymerization is said to produce "ultra-high molecular weight polyolefin drag reducers [that] are significantly larger (molecular weight basis) than the best molecular weights made by solution polymerization." See U.S. Pat. No. 5,504,132. Preferred DRA's for removal according to the process described herein are made by solution polymerization.

Without limiting the invention to a specific theory or mechanism of action, the very large polyalpha olefins made by bulk polymerization may be more difficult to adsorb onto and retain on the carbonaceous removal agents. In contrast, the polyalpha olefins made by solution polymerization may be more readily adsorbable onto the removal agents, and more readily retained by the removal agents.

Drag reducer additives are generally unsheared, partially sheared, or fully sheared. An additive that is fully sheared is one that is degraded in molecular weight to the maximum extent possible using high shear devices such as pumps, static mixers, etc. Commercially available drag reducer additives include, but are not necessarily limited to, CDR® Flow Improver and REFINED POWER™ manufactured by Conoco Specialty Products, Inc., EN-660 Flow Improver, manufactured by Energy 2000 LLC, and FLO® XS and FLO® XL, manufactured by Baker Petrolite. In a preferred embodiment, the drag reducer additive is FLO® XS and equivalents thereof.

The exact mechanism by which a drag reducer additive reduces drag in flowing liquid hydrocarbons is not completely known. However, a drag reducer additive apparently alters the turbulent flow regime of the liquid hydrocarbons. In a pipeline, this flow regime is comprised of at least three regions. At the center of the pipe is a turbulent core, which is the largest region and includes most of the fluid in the pipe. This is the zone of eddy currents and random motions for which turbulent flow is named. Nearest to the pipe line wall is the laminar sublayer. In this zone, the fluid moves laterally in "sheets". Between the laminar layer and the turbulent core lies the "buffer zone". It appears that much of the turbulence which exists in turbulent flow develops when a portion of the laminar sublayer, called a "streak", moves up to the buffer zone, where it begins to vortex and oscillate, finally breaking up and throwing fluid into the core. This ejection of fluid into the core is called a "burst". The burst creates the turbulence in the core, and energy is wasted in different directions. Drag reducer additive appears to interfere with the bursting process and prevent or reduce the degree of turbulence by stretching in the flow, absorbing the energy in the streak, and thereby preventing bursts.

As liquids containing drag reducer additive travel through pumps, pipelines and other equipment, the drag reducer additive typically degrades through shearing action, resulting in a reduction in the molecular weight of the drag reducer additive. The degraded drag reducer additive is generally sheared or partially sheared drag reducer additive. Upon reaching the ultimate destination, liquid hydrocarbon fuels that have been shipped using drag reducer additive may contain a significant amount of drag reducer additive, including that in the sheared and partially sheared form.

Removal Agents for Removing DRA from Fuels

The present application is based on the surprising finding that selected activated carbons and graphites, particularly selected graphites, are much more effective than others as removal agents for binding and removing drag reducer additive from fuels, preferably motor gasoline and jet fuels, most preferably jet fuels. The superiority has been demonstrated in unsheared DRA known as Baker Petrolite FLO® XS.

Without limiting the application to a particular theory or mechanism of operation, the more active removal agents are believed to comprise ducts or pores having a hydrophobic/hydrophilic property that provides a chemical attraction to pendant groups on the drag reducer additive. The chemical attraction is believed to bring the pendant groups on the drag reducer additive into proximity and orientation with the pore surface of the agent, thereby immobilizing the pendant groups. Because many pendant groups on a given drag reducer molecule are simultaneously immobilized, the drag reducer molecule is strongly immobilized.

Without limiting the claims to a particular mechanism or theory of action, the effective activated carbons and graphites are believed to be porous materials comprising pores having a hydrophobic/hydrophilic property that is compatible with or provides a chemical attraction to pendant groups of the particular drag reducer additive. The specific activated carbons and graphites may be in the form of crushed particles or granules, powder, cylinders, globules, fibers, or honeycombs. Preferred agents are in the form of particles or granules. Most preferred agents are in powder or granule form.

Activated Carbons

Suitable activated carbons are commercially available, for example, from Allchem Industries, Inc., Beta Chemicals, Calgon, Coyne Chemical Co., Elf Atochem North America, Inc. (Performance Products), R. W. Greef & Co, Inc., Kingshine Chemical Co., Ltd., Mays Chemical Co., Inc., Mitsubishi International Corp. (Industrial Specialty Chemicals Div.), Spectrum Chemical Mfg. Corp., Norit and others. When added (in increments with agitation) to a fuel mixture containing a preferred unsheared drag reducer additive of about 8–12 ppm polymer concentration, more preferably about 9–11 ppm polymer concentration, most preferably about 10 ppm polymer concentration, suitable activated carbons attain a % polymer removal of about 20% or more; preferably about 30% or more; more preferably at least about 40% or more, at about 1 g activated carbon/100 ml fuel. This equates to a % adsorption capacity of about 0.014% or more, preferably about 0.02% or more, most preferably about 0.03% or more. When added (in increments with agitation) to a fuel mixture containing a preferred sheared drag reducer additive of about 8–12 ppm polymer concentration, more preferably about 9–11 ppm polymer concentration, most preferably about 10 ppm polymer concentration, suitable activated carbons attain a % polymer removal of about 20% or more; preferably about 25% or more; more preferably about 30% or more, at about 1 g activated carbon/100 ml fuel. This equates to a % adsorption capacity of about 0.018% or more, preferably about 0.025% or more, more preferably about 0.03% or more.

Commercially viable activated carbons, which have been demonstrated to be suitable to remove Baker Petrolite FLO® XS and equivalents thereof include, but are not necessarily limited to, CALGON ADP, CALGON COLORSORB, CALGON WPX, NORIT A SUPRA, NORIT CA 1, NORIT FGD, NORIT HDB, SXO POWDER, and CARBON 5565. Preferred activated carbons demonstrated to be useful for removing Baker Petrolite FLO® XS and equivalents thereof include, but are not necessarily limited to CALGON WPX, NORIT A SUPRA, NORIT CA 1, NORIT FGD, NORIT HDB, SXO POWDER and CARBON 5565. Most preferred activated carbons demonstrated to be useful for removing Baker Petrolite FLO® XS and equivalents thereof include, but are not necessarily limited to NORIT A SUPRA, NORIT CA1, NORIT FGD, and NORIT HDB.

Preferred Graphites

Most preferred carbonaceous materials are graphites. Graphite is a crystalline form of carbon found as a naturally occurring mineral in many locations around the world. Graphite can be amorphous ("amorphous graphite"). Graphite also can have a perfect basal cleavage which, coupled with its extreme softness, gives it an oily, slippery feel, such graphites include, but are not necessarily limited to natural graphite, synthetic graphite, and expanded graphite. Each of these graphite types is commercially available in various forms, including, crystalline lumps, crystalline large flakes, crystalline medium flakes, crystalline small flakes, and powder form. Artificial graphite can be manufactured from petroleum coke and is primarily used to make electrodes. The virgin by-product of such electrode production has a carbon content as high as 99.9%, and can be a relatively inexpensive source of graphite agent, to highly refined natural graphite. Suitable candidate graphites are commercially available, for example, from Asbury Carbons, Inc., Asbury, N.J.; Superior Graphite Co., Chicago, Ill.; Stanford Materials Corporation, Aliso Viejo, Calif.; and others.

Preferred graphites comprise graphite powders or granular graphite particulates. The granular graphite particulates have an average diameter of from about 0.01 microns to about 10,000 microns; preferably from about 0.1 microns to about 1,000 microns; most preferably about 1 micron to about 100 microns. Preferred graphites have a porosity sufficient to provide an adsorption capacity of about 0.01 wt. % or more, preferably about 0.03 wt. % or more, most preferably about 0.04 wt %, when added to a preferred drag reducer additive. Suitable and preferred graphites are commercially available from Superior Graphite Company. Preferred graphite products comprise, but are not necessarily limited to, purified carbon, natural graphite, silica (crystalline quartz), and synthetic graphite.

When added (in increments with agitation) to a fuel mixture containing a preferred unsheared drag reducer additive of about 8–12 ppm polymer concentration, more preferably about 9–11 ppm polymer concentration, most preferably about 10 ppm polymer concentration, suitable graphites attain a % polymer removal of about 30% or more; preferably about 40% or more; more preferably at least about 50% or more, at about 1 g graphite/100 ml fuel. This equates to a % adsorption capacity of about 0.02% or more, more preferably about 0.03% or more, most preferably about 0.04% or more. When added (in increments with agitation) to a fuel mixture containing a preferred sheared drag reducer additive of about 8–12 ppm polymer concentration, more preferably about 9–11 ppm polymer concentration, most preferably about 10 ppm polymer concentration, suitable graphites attain a % polymer removal of at least about 25%; more suitably at least about 30%; most suitably at least about 35%, at about 1 g graphite/100 ml fuel. This equates to a % adsorption capacity of about 0.02%, more preferably about 0.025%, most preferably about 0.03%.

Graphites that demonstrated commercial viability for adsorbing unsheared and sheared BAKER PETROLITE FLO® XS and equivalents included GRAPHITE 2126, GRAPHITE 2139, GRAPHITE 3726, GRAPHITE 3739, GRAPHITE 5526, GRAPHITE 5539, GRAPHITE 9026, GRAPHITE 9039, and GRAPHITE GA-17, available from Superior Graphite Co. The foregoing graphites exhibited an adsorption capacity for unsheared and sheared BAKER PETROLITE FLO® XS of about 0.01 wt % or more.

Preferred commercially available graphites for adsorbing unsheared BAKER PETROLITE FLO® XS and equivalents included GRAPHITE 2126, GRAPHITE 2139, GRAPHITE 3726, GRAPHITE 3739, GRAPHITE 5539, GRAPHITE 9039, and GRAPHITE GA-17. The foregoing graphites exhibited an adsorption capacity for unsheared BAKER PETROLITE FLO® XS of about 0.02 wt % or more. Preferred commercially available graphites for adsorbing sheared BAKER PETROLITE FLO® XS and equivalents included GRAPHITE 2126, GRAPHITE 2139, GRAPHITE 3726, GRAPHITE 3739, GRAPHITE 9026, and GRAPHITE 9039. The foregoing graphites exhibited an adsorption capacity for sheared BAKER PETROLITE FLO® XS of about 0.018 wt % or more.

Even more preferred commercially available graphites for adsorbing unsheared BAKER PETROLITE FLO® XS and equivalents included GRAPHITE 2139, GRAPHITE 3726, GRAPHITE 3739, GRAPHITE 5539, GRAPHITE 9039, and GRAPHITE GA-17. The foregoing graphites exhibited an adsorption capacity for unsheared BAKER PETROLITE FLO® XS of about 0.03 wt % or more.

Most preferred graphites, particularly for adsorbing unsheared BAKER PETROLITE FLO® XS and equivalents thereof, include but are not necessarily limited to GRAPHITE 2139 and GRAPHITE 3739. The foregoing graphites exhibited an adsorption capacity for unsheared BAKER PETROLITE FLO® XS of about 0.04 wt % or more. Most preferred graphites, particularly for adsorbing sheared BAKER PETROLITE FLO® XS and equivalents thereof, include but are not necessarily limited to GRAPHITE 3726 and GRAPHITE 3739. The foregoing graphites exhibited an adsorption capacity for sheared BAKER PETROLITE FLO® XS of about 0.025 wt % or more.

Removal of Drag Reducer Additive from Liquid Hydrocarbon Fuels

It may be desirable simply to subject all of a given fuel at a given storage or transport site to a DRA removal procedure. This would be particularly effective if all the DRA in use was removable by carbonaceous materials. In fact, it would even be most preferable to use as DRA in fuels only materials known to be removable by carbonaceous materials. Or it may be desirable to test for the presence of DRA before incurring the expense of removal.

Once preferred carbonaceous materials, preferably graphite removal agents have been identified, the activated carbon and/or graphite(s) may be used to remove the drag reducer additive from a given liquid hydrocarbon fuel, preferably motor gasoline or jet fuel, most preferably jet fuel. Alternately, a given sample of hydrocarbon fuel is analyzed for DRA by gel permeation chromatography (GPC).

When it is desired to remove DRA from a given fuel, one or more effective carbonaceous materials, preferably selected activated carbons, more preferably graphite(s) are incorporated into a system for filtering the DRA/fuel mixture and for removing drag reducer additive from that mixture. The filter may be in any suitable form and may be installed in a variety of locations. Suitable locations include, but are not necessarily limited to a pipeline to a fuel terminal, a delivery system between a fuel terminal and a tanker truck, a delivery system between two different tanker trucks, a delivery system from a tanker truck to a storage tank or to an engine, and, actually as a component of the engine, itself. In one embodiment, the filter comprises a component of a fuel delivery system from a tanker truck to a jet engine. The filter may be used in substantially any type of delivery system. In each method, the graphites may or may not be heated. Heating removes any water, if any is adsorbed on the graphite.

Due to the difficulty in providing for incremental addition and agitation in most commercial situations, it may be preferred to simply pass the liquid hydrocarbon fuel through a bed of the carbonaceous materials, preferably selected activated carbons, more preferably graphite(s), until the removal rate is so low that the carbonaceous materials must be replaced. In one embodiment, the filtering system provides for agitation of the DRA/fuel mixture as incremental additions of a given carbonaceous material, preferably a selected activated carbon(s), more preferably graphite(s) are added to the DRA/fuel mixture. This procedure is sometimes herein referred to as the "gradual addition and stirring" method or "Grad Add/Stir" method. This is a preferred method for more viscous hydrocarbon fuels such as jet fuel.

Civilian aircraft generally are serviced in hangers at airports. Military aircraft are serviced on the flight line, where a row of aircraft are parked away from a maintenance terminal and nearer to the runway, to be ready for mobilization. The distance from the flight line to the maintenance terminals may be as much as one mile. Servicing of aircraft, particularly military aircraft, typically is performed by shuttling service vehicles out to the flight line from the maintenance terminal where they perform the requisite service. Periodically, the servicing vehicles return to the maintenance terminal to themselves be refueled or for other servicing.

An example of how the system would be incorporated into a known fuel delivery system is described in U.S. patent application Ser. No. 10/124,974, filed on Apr. 18, 2002, incorporated herein by reference. Briefly, the fuel delivery system comprises: (1) a tank of a refueling truck, (2) a transfer hose, (3) a bracket for storing the hose, (4) a manual pump, (5) a filter device, (6) a drain connected to the transfer hose at one end, and (7) a shutoff valve. The filter device comprising the removal agent of the present application may be inserted either in series or in parallel with these one-way filters. Preferably, a filter device, such as a canister or cartridge of the removal agent(s), is placed downstream of the one-way filters in order to improve efficiency and longevity of the operation.

The application will be better understood with reference to the following examples, which are illustrative only:

EXAMPLE 1

The Grad Add/Stir method was used in this example. About 100 ml of jet fuel comprising about 8.36 ppm of FLO® XS-unsheared DRA (manufactured by Baker Petrolite) was stirred with a magnetic stir bar, to create a moderate vortex. Increments of about 0.02 to about 0.1 gram of a removal agent were placed in the agitating DRA/jet fuel mixture, while stirring, until a total of about 1.0 g had been added. The stirring was continued for approximately two to three minutes. The sample was allowed to settle for about 5 minutes. The carbon was removed from the mixture by filtration with a Whatman 8 micron filter. The mixture was then tested for polymer concentration.

The polymer adsorption of removal agents increased with graphite as compared to activated carbon. Table 1 (in Example 2) summarizes the % DRA adsorbed for both an activated carbon group (34 samples), and a graphite group (9 samples). FIG. 1 is a graphical representation of the effectiveness of graphites to remove unsheared DRA from jet fuel. Table 1 further summarizes the % adsorption capacity for both an activated carbon group, and a graphite group. For unsheared DRA, the % adsorption capacity of a given carbon=(0.000678)*(% polymer removed). This formula is derived using the initial polymer concentration, volume of DRA/fuel used in the experiment, weight of carbon used in the experiment, and density of the DRA/fuel used.

As shown in FIG. 1, graphites are more effective at removing unsheared polymer than activated carbons. The highest removal effectiveness of the 43 removal agents tested was 58.20% (with "Graphite 3739"), provided by Superior Graphite Company, which corresponds to a polymer adsorption capacity of 0.04% (wt).

EXAMPLE 2

The Quick Add/Stir method was used in this example. About 100 ml of jet fuel comprising about 8.36 ppm of FLO® XS-unsheared DRA (manufactured by Baker Petrolite) was stirred with a magnetic stir bar, to create a moderate vortex. Once the removal agent had cooled, about 1.0 g of the removal agent was placed in the agitating DRA/jet fuel mixture, while stirring. The stirring was continued for approximately two to three minutes. The sample was allowed to settle for about 5 minutes. The carbon was removed from the mixture by filtration with a Whatman 8 micron filter. The mixture was then tested for polymer concentration.

Figure 2:
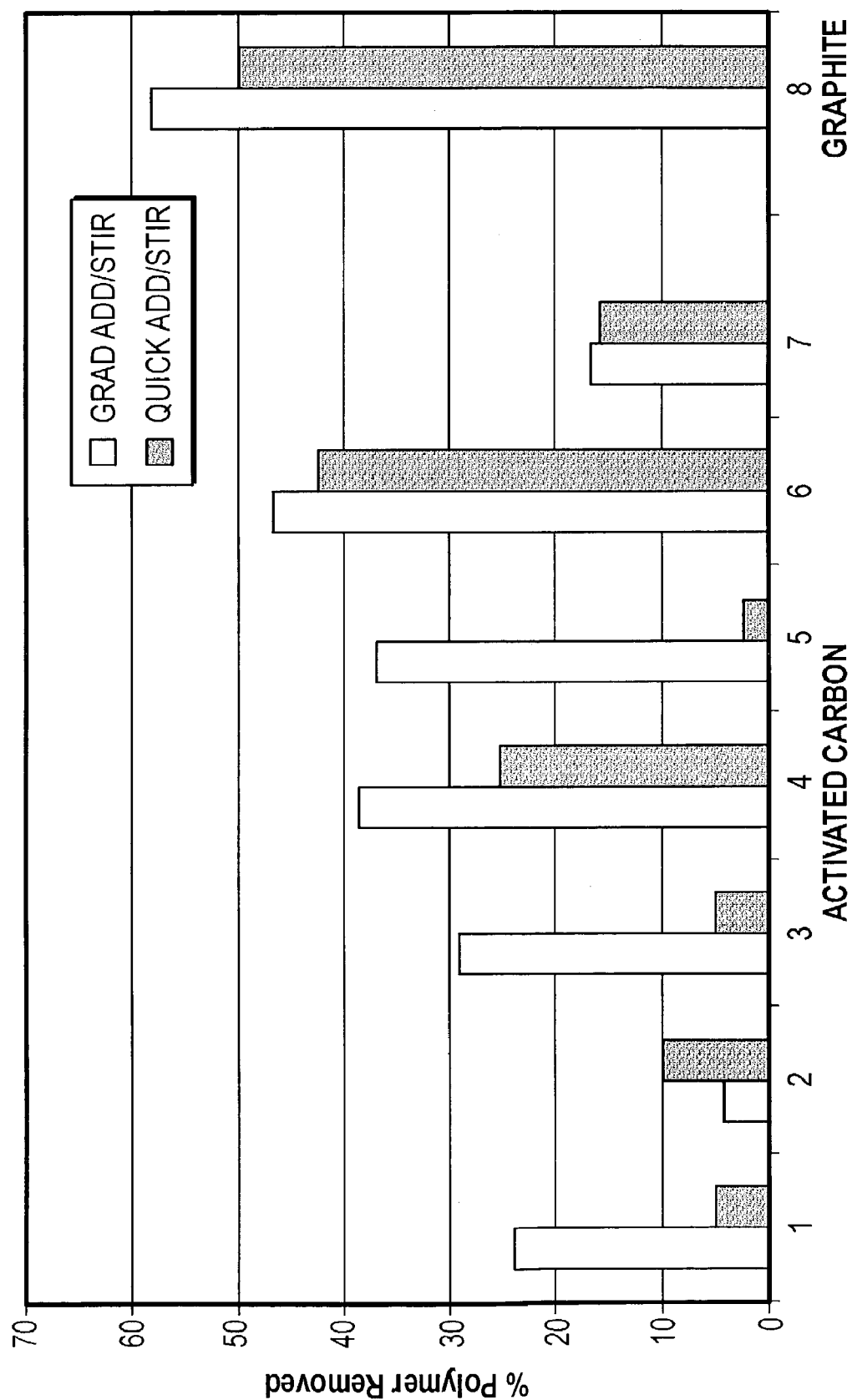
FIG. 2 is a graph of % Polymer Removed vs. Carbon (activated carbons and graphites) used to remove unsheared FLO® XS polymer from jet fuel for both Grad Add/Stir and Quick Add/Stir methods using the Grad Add/Stir method.

The polymer adsorption of removal agents increased with graphite as compared to activated carbon. Table 1 summarizes the % DRA adsorbed for both an activated carbon group (7 samples), and a graphite group (1 sample). The highest removal effectiveness of the 8 removal agents tested was 49.90% (with "Graphite 3739"), which corresponds to a polymer adsorption capacity of 0.034% (wt). FIG. 2 compares the effectiveness of removing DRA using the Grad Add/Stir and Quick Add/Stir methods for the 8 commonly tested removal agents. The Grad Add/Stir method gave superior results in 5 of the 8 carbons tested. The Quick Add/Stir method gave superior results in 3 of the 8 carbons tested. FIG. 2 further demonstrates that graphite is more effective at DRA removal than activated carbon, regardless of the method employed.

The removal agents listed in Table 1 are derived from numerous sources, including wood, coconut and other shells, peat, bituminous coal, lignite coal, and anthracite coal. Each carbon source material differs in surface area, pore size, density, and strength characteristics.

TABLE 1

| Sample | % Polymer Removal (Grad Add/Stir Method) FLO ® XS-Unsheared | % Adsorption Capacity (Grad Add/Stir Method) FLO ® XS-Unsheared | % Polymer Removal (Quick Add/Stir Method) FLO ® XS-Unsheared | % Adsorption Capacity (Quick Add/Stir Method) FLO ® XS-Unsheared |
|---|---|---|---|---|
| Activated Carbon | | | | |
| (1) Calgon ADP | 22.40 | 0.015 | | |
| (2) Calgon APL | 2.43 | 0.002 | | |
| (3) Calgon BL | 6.44 | 0.004 | | |
| (4) Calgon C | 6.68 | 0.005 | | |
| (5) Calgon Colorsorb | 23.70 | 0.016 | 4.78 | 0.003 |
| (6) Calgon RB | 4.13 | 0.003 | 9.81 | 0.070 |
| (7) Calgon RC | 0.00 | 0.00 | | |
| (8) Calgon WPH | 6.93 | 0.005 | | |
| (9) Calgon WPL | 4.98 | 0.003 | | |
| (10) Calgon WPX | 29.20 | 0.020 | 5.02 | 0.003 |
| (11) Darco G-60 | 9.60 | 0.007 | | |
| (12) Darco S-51 | 9.48 | 0.006 | | |
| (13) Norit A Supra | 38.80 | 0.026 | 25.20 | 0.020 |
| (14) Norit CAl | 37.10 | 0.025 | 2.27 | 0.002 |
| (15) Norit CASPF | 18.30 | 0.012 | | |
| (16) Norit E Supra | 0.00 | 0.00 | | |
| (17) Norit FGD | 47.00 | 0.032 | 42.60 | 0.030 |
| (18) Norit HDB | 36.10 | 0.025 | | |
| (19) Norit KB | 16.50 | 0.011 | 15.70 | 0.011 |
| (20) Norit PAC200 | 0.00 | 0.00 | | |
| (21) Norit SX Plus | 0.00 | 0.00 | | |
| (22) Norit SX 4 | 2.19 | 0.002 | | |
| (23) Aquacarb 1230C | 20.20 | 0.014 | | |
| (24) Aquacarb 1230CAW | 4.98 | 0.003 | | |
| (25) Aquacarb 1240 | 4.01 | 0.003 | | |
| (26) Aquacarb 1240AW | 3.77 | 0.003 | | |
| (27) Aguapac 800 | 14.00 | 0.010 | | |
| (28) Bevcarb 800 | 0.00 | 0.00 | | |
| (29) Ultracarb 1240 | 14.60 | 0.010 | | |
| (30) Chemcarb C25 | 3.65 | 0.003 | | |
| (31) PAC 2000-600 | 17.90 | 0.012 | | |
| (32) PAC 2000-900 | 7.90 | 0.005 | | |
| (33) SX0 Powder | 35.80 | 0.024 | | |
| (34) Carbon 5565 | 33.40 | 0.023 | | |
| Graphite | | | | |
| (35) Graphite 2126 | 29.30 | 0.020 | | |
| (36) Graphite 2139 | 52.60 | 0.040 | | |
| (37) Graphite 3726 | 37.20 | 0.030 | | |
| (38) Graphite 3739 | 58.20 | 0.040 | 49.90 | 0.034 |

TABLE 1-continued

| Sample | % Polymer Removal (Grad Add/Stir Method) FLO® XS-Unsheared | % Adsorption Capacity (Grad Add/Stir Method) FLO® XS-Unsheared | % Polymer Removal (Quick Add/Stir Method) FLO® XS-Unsheared | % Adsorption Capacity (Quick Add/Stir Method) FLO® XS-Unsheared |
|---|---|---|---|---|
| (39) Graphite 5526 | 14.30 | 0.010 | | |
| (40) Graphite 5539 | 43.60 | 0.030 | | |
| (41) Graphite 9026 | 20.40 | 0.014 | | |
| (42) Graphite 9039 | 37.90 | 0.030 | | |
| (43) Graphite GA-17 | 43.50 | 0.030 | | |

Based on the foregoing, a gradual or incremental add/stir procedure is more efficient in removing DRA from more viscous hydrocarbon fuels, such as jet fuel.

EXAMPLE 3

The Grad Add/Stir method was used in this example. About 100 ml of jet fuel comprising about 8.36 ppm of FLO® XS-sheared DRA (manufactured by Baker Petrolite) was stirred with a magnetic stir bar, to create a moderate vortex. Increments of about 0.02 to about 0.1 gram of a removal agent were placed in the agitating DRA/jet fuel mixture, while stirring, until a total of about 1.0 g had been added. The stirring was continued for approximately two to three minutes. The sample was allowed to settle for about 5 minutes. The carbon was removed from the mixture by filtration with a Whatman 8 micron filter. The mixture was then tested for polymer concentration.

Figure 3:
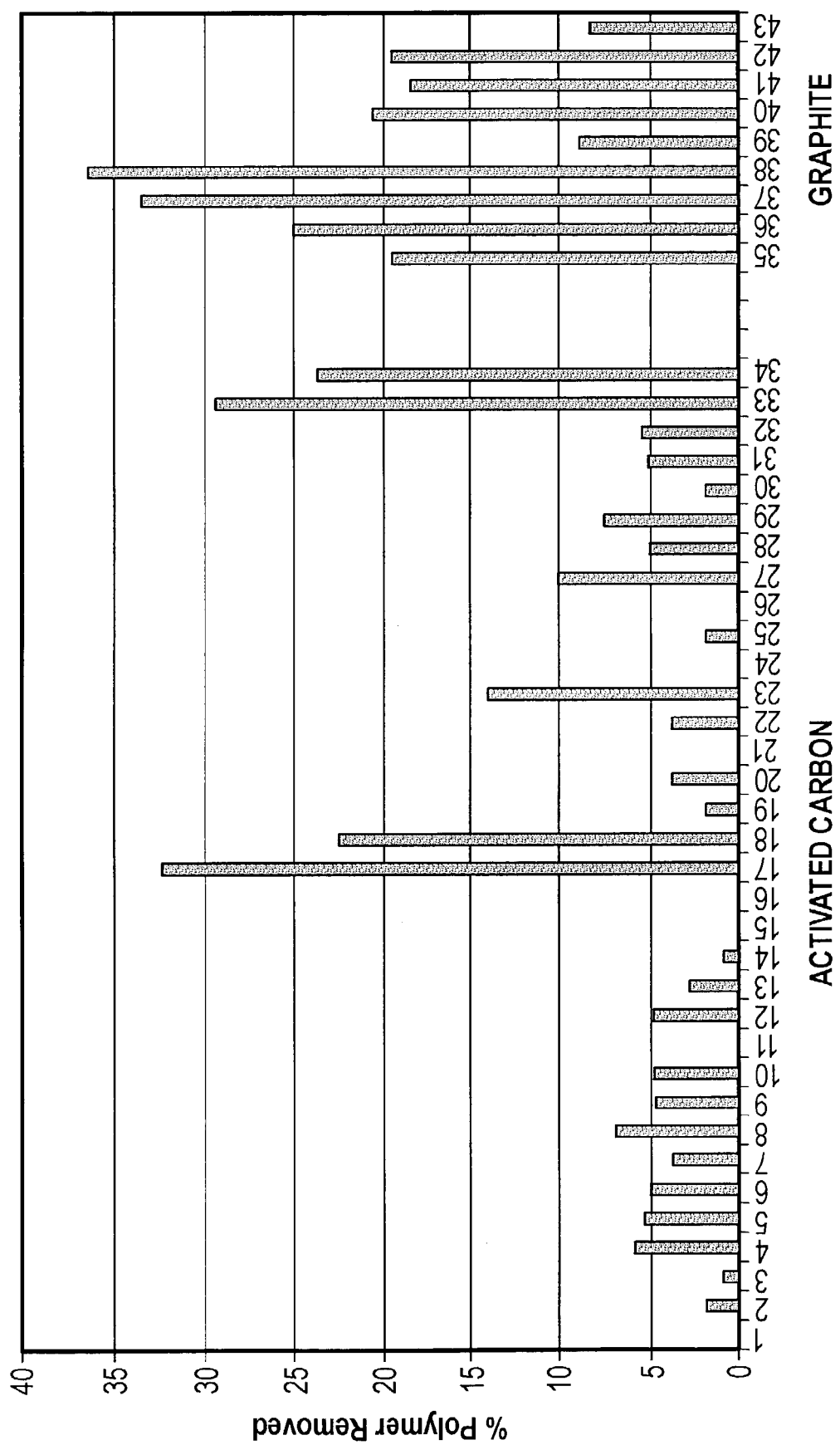
FIG. 3 is a graph of % Polymer Removed vs. Carbon (activated carbons and graphites) used to remove sheared FLO® XS polymer from jet fuel using the Grad Add/Stir method.

The polymer adsorption of removal agents increased with graphite as compared to activated carbon. Table 2 (in Example 4) summarizes the % DRA adsorbed for both an activated carbon group (34 samples), and a graphite group (9 samples). FIG. 3 is a graphical representation of the effectiveness of graphites to remove sheared DRA from jet fuel. Table 2 further summarizes the % adsorption capacity for both an activated carbon group, and a graphite group. For sheared DRA, the % adsorption capacity of a given carbon= (0.000857)*(% polymer removed). This formula is derived using the initial polymer concentration, volume of DRA/fuel used in the experiment, weight of carbon used in the experiment, and density of the DRA/fuel used.

As shown in FIG. 3, graphites are more effective at removing sheared polymer than activated carbons. The highest removal effectiveness of the 43 removal agents tested was 36.30% (with "Graphite 3739"), which corresponds to a polymer adsorption capacity of 0.031% (wt).

EXAMPLE 4

The Quick Add/Stir method was used in this example. About 100 ml of jet fuel comprising about 8.36 ppm of FLO® XS-sheared DRA was stirred with a magnetic stir bar, to create a moderate vortex. Once the removal agent had cooled, about 1.0 g of the removal agent was placed in the agitating DRA/jet fuel mixture, while stirring. The stirring was continued for approximately two to three minutes. The sample was allowed to settle for about 5 minutes. The carbon was removed from the mixture by filtration with a Whatman 8 micron filter. The mixture was then tested for polymer concentration.

Figure 4:
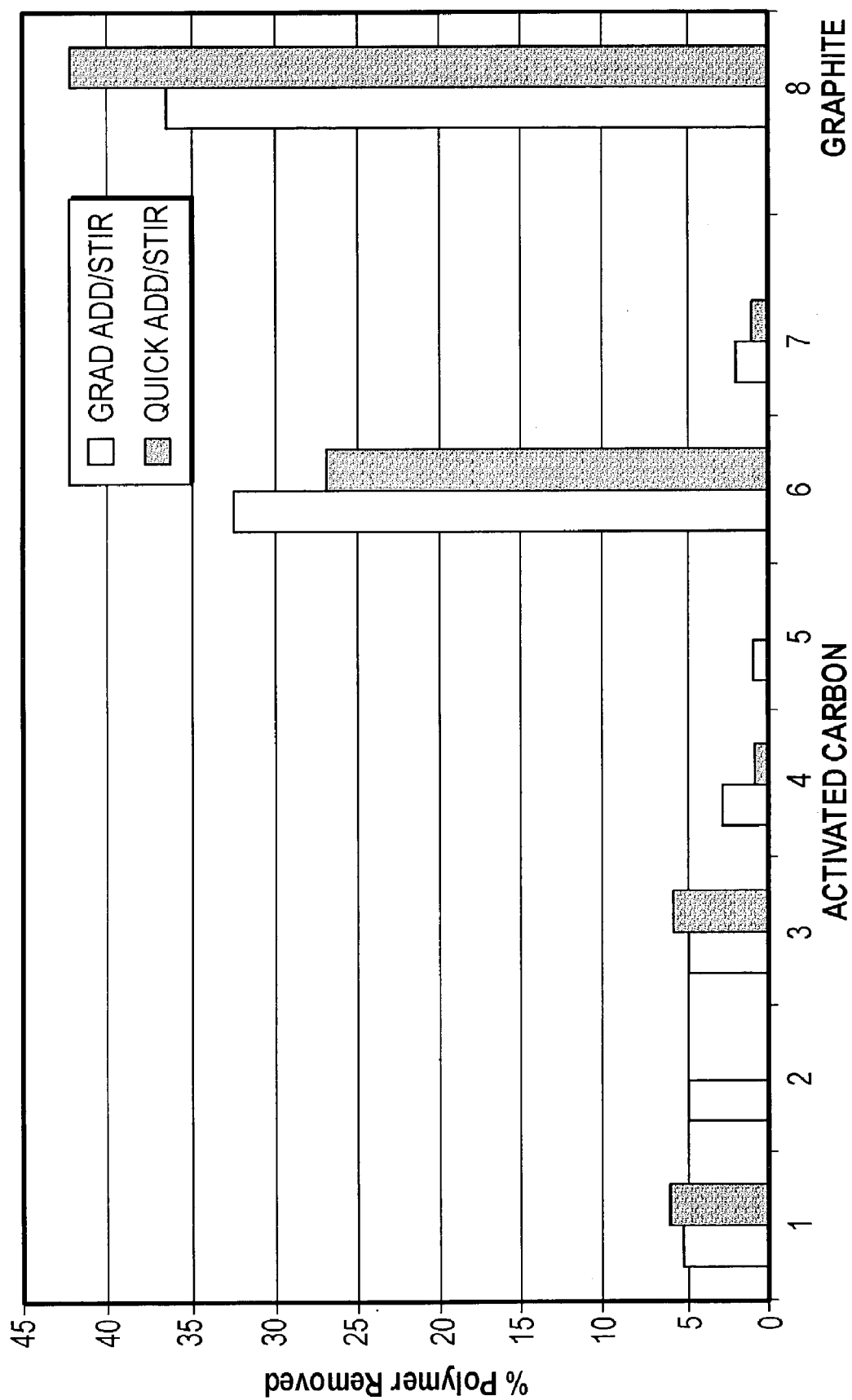
FIG. 4 is a graph of % Polymer Removed vs. Carbon (activated carbons and graphites) used to remove sheared FLO® XS polymer from jet fuel for both Grad Add/Stir and Quick Add/Stir methods.

The polymer adsorption of removal agents increased with graphite as compared to activated carbon. Table 2 summarizes the % DRA adsorbed for both an activated carbon group (7 samples), and a graphite group (1 sample). The highest removal effectiveness of the 8 removal agents tested was 42.10% (with "Graphite 3739"), which corresponds to a polymer adsorption capacity of 0.040% (wt). FIG. 4 compares the effectiveness of removing DRA using the Grad Add/Stir and Quick Add/Stir methods for the 8 commonly tested removal agents. The Grad Add/Stir method gave superior results in 5 of the 8 carbons tested. The Quick Add/Stir method gave superior results in 3 of the 8 carbons tested. FIG. 4 further demonstrates that graphite is more effective at DRA removal than activated carbon, regardless of the method employed.

Figure 5:
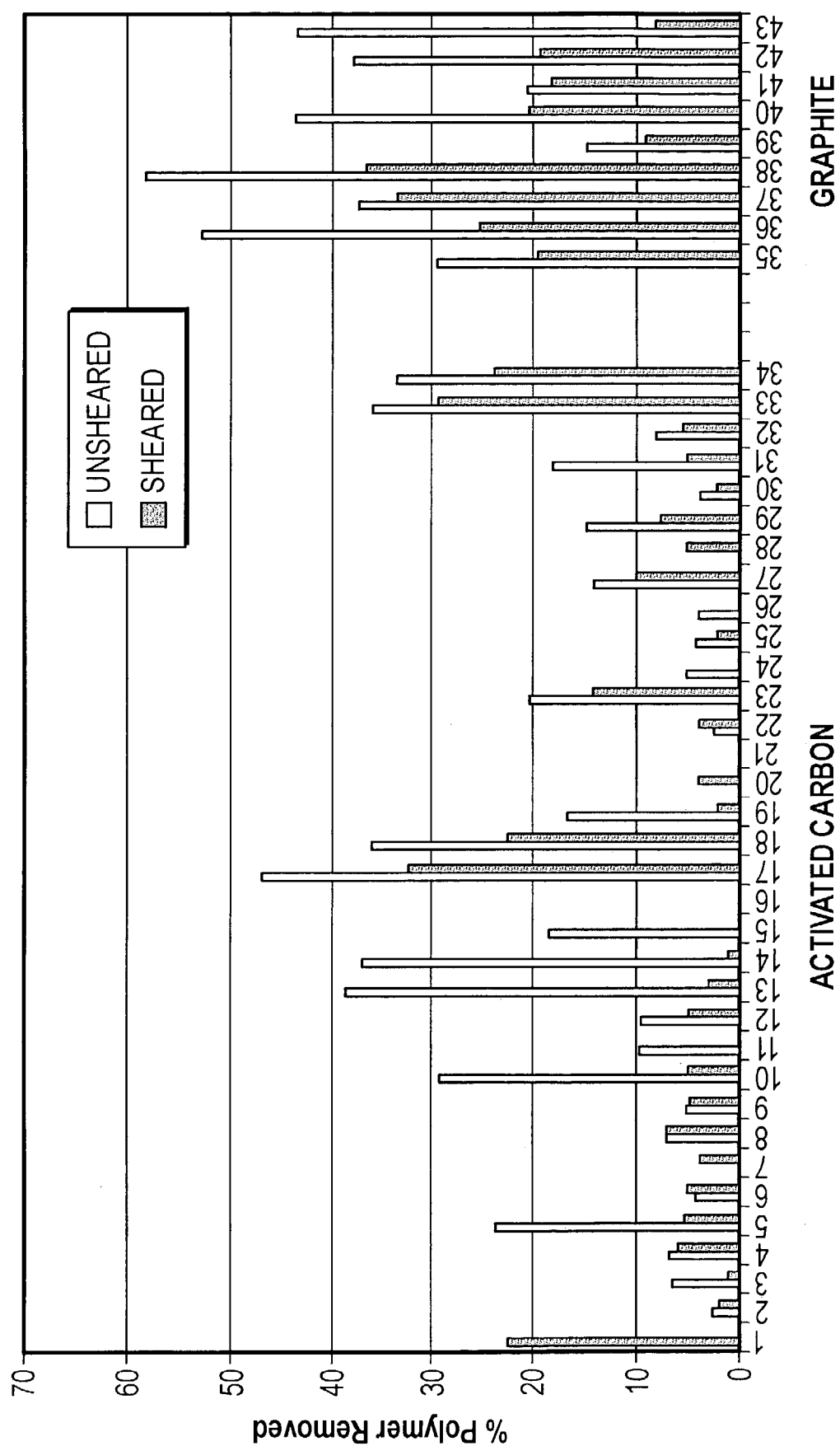
FIG. 5 is a graph of % Polymer Removed vs. Carbon (activated carbons and graphites) used to remove FLO® XS polymer from jet fuel for Unsheared vs. Sheared FLO® XS polymer using the Grad Add/Stir method.

FIG. 5 demonstrates the effectiveness of the removal agents to remove both sheared and unsheared FLO® XS from jet fuel. All removal agents perform better removing unsheared polymer over sheared polymer. Only the most effective removal agents at removing unsheared polymer were effective at removing sheared polymer.

TABLE 2

| Sample | % Polymer Removal (Grad Add/Stir Method) FLO® XS-Sheared | % Adsorption Capacity (Grad Add/Stir Method) FLO® XS-Sheared | % Polymer Removal (Quick Add/Stir Method) FLO® XS-Sheared | % Adsorption Capacity (Quick Add/Stir Method) FLO® XS-Sheared |
|---|---|---|---|---|
| Activated Carbon | | | | |
| (1) Calgon ADP | 00.00 | 00.00 | | |
| (2) Calgon APL | 1.900 | 0.002 | | |

TABLE 2-continued

| Sample | % Polymer Removal (Grad Add/Stir Method) FLO ® XS-Sheared | % Adsorption Capacity (Grad Add/Stir Method) FLO ® XS-Sheared | % Polymer Removal (Quick Add/Stir Method) FLO ® XS-Sheared | % Adsorption Capacity (Quick Add/Stir Method) FLO ® XS-Sheared |
|---|---|---|---|---|
| (3) Calgon BL | 00.95 | 0.001 | | |
| (4) Calgon C | 5.900 | 0.010 | | |
| (5) Calgon Colorsorb | 5.330 | 0.005 | 6.100 | 0.010 |
| (6) Calgon RB | 4.950 | 0.004 | 00.00 | 00.00 |
| (7) Calgon RC | 3.810 | 0.003 | | |
| (8) Calgon WPH | 6.950 | 0.006 | | |
| (9) Calgon WPL | 4.760 | 0.004 | | |
| (10) Calgon WPX | 4.860 | 0.004 | 5.81 | 0.005 |
| (11) Darco G-60 | 00.00 | 00.00 | | |
| (12) Darco S-51 | 4.860 | 0.004 | | |
| (13) Norit A Supra | 2.860 | 0.003 | 0.95 | 0.001 |
| (14) Norit CAl | 0.950 | 0.001 | 00.00 | 00.00 |
| (15) Norit CASPF | 00.00 | 00.00 | | |
| (16) Norit E Supra | 00.00 | 00.00 | | |
| (17) Norit FGD | 32.40 | 0.030 | 26.70 | 0.023 |
| (18) Norit HDB | 22.50 | 0.020 | | |
| (19) Norit KB | 1.900 | 0.002 | 0.95 | 0.001 |
| (20) Norit PAC 200 | 3.810 | 0.003 | | |
| (21) Norit SX Plus | 00.00 | 00.00 | | |
| (22) Norit SX 4 | 3.810 | 0.003 | | |
| (23) Aquacarb 1230C | 14.00 | 0.012 | | |
| (24) Aquacarb 1230CAW | 00.00 | 00.00 | | |
| (25) Aquacarb 1240 | 1.900 | 0.002 | | |
| (26) Aquacarb 1240AW | 00.00 | 00.00 | | |
| (27) Aquapac 800 | 10.00 | 0.010 | | |
| (28) Bevcarb 800 | 4.950 | 0.004 | | |
| (29) Ultracarb 1240 | 7.430 | 0.010 | | |
| (30) Chemcarb C25 | 1.900 | 0.002 | | |
| (31) PAC 2000-600 | 4.950 | 0.004 | | |
| (32) PAC 2000-900 | 5.330 | 0.005 | | |
| (33) SX0 Powder | 29.30 | 0.030 | | |
| (34) Carbon 5565 | 23.60 | 0.020 | | |
| Graphite | | | | |
| (35) Graphite 2126 | 19.30 | 0.020 | | |
| (36) Graphite 2139 | 25.00 | 0.021 | | |
| (37) Graphite 3726 | 33.40 | 0.030 | | |
| (38) Graphite 3739 | 36.30 | 0.031 | 42.10 | 0.040 |
| (39) Graphite 5526 | 8.670 | 0.007 | | |
| (40) Graphite 5539 | 20.40 | 0.017 | | |
| (41) Graphite 9026 | 18.10 | 0.020 | | |
| (42) Graphite 9039 | 19.20 | 0.020 | | |
| (43) Graphite GA-17 | 7.990 | 0.007 | | |

Persons of ordinary skill in the art will recognize that many modifications may be made to the present application without departing from the spirit and scope of the present application. The embodiment described herein is meant to be illustrative only and should not be taken as limiting the application.

I claim:

1. A method of removing drag reducer additive from liquid hydrocarbon fuel, said method comprising:
   providing contaminated liquid hydrocarbon fuel comprising a concentration of drag reducer additive (DRA);
   contacting said contaminated liquid hydrocarbon fuel with a quantity of one or more graphite effective to substantially reduce said concentration of DRA, said contacting occurring under conditions effective to produce clean liquid hydrocarbon fuel wherein said graphite comprises an adsorption capacity for said DRA of about 0.01 wt. % or more at from about 8 to about 12 ppm DRA concentration and at about 1 g graphite/100 ml fuel, said DRA being selected from the group consisting of sheared DRA, partially sheared DRA, and unsheared DRA.

2. The method of claim 1 wherein said graphite comprises an adsorption capacity for DRA of about 0.02 wt. % or more at from about 8 to about 12 ppm DRA concentration and at about 1 g graphite/100 ml fuel.

3. The method of claim 1 wherein said graphite comprises an adsorption capacity for sheared DRA of about 0.025 wt. % or more at from about 8 to about 12 ppm DRA concentration and at about 1 g graphite/100 ml fuel.

4. The method of claim 1 wherein said graphite comprises an adsorption capacity for said unsheared DRA of about 0.04 wt. % or more at from about 8 to about 12 ppm DRA concentration and at about 1 g graphite/100 ml fuel.

5. A method of removing drag reducer additive from liquid hydrocarbon fuel, said method comprising:
   providing contaminated liquid hydrocarbon fuel comprising a concentration of drag reducer additive (DRA) selected from the group consisting of sheared DRA, partially sheared DRA, and unsheared DRA;
   contacting said contaminated liquid hydrocarbon fuel with a quantity of one or more graphite effective to substantially reduce said concentration of DRA, said contacting occurring under conditions effective to produce a clean liquid hydrocarbon fuel wherein said graphite produces a % removal for said DRA of about 25% or more at from 8 to about 12 ppm DRA concentration and at about 1 g graphite/100 ml fuel.

6. The method of claim 5 wherein said graphite produces a % removal for DRA of about 30% or more at from about 8 to about 12 ppm DRA concentration and at about 1 g graphite/100 ml fuel, said DRA being selected from the group consisting of sheared and unsheared DRA.

7. The method of claim 5 wherein said DRA comprises sheared DRA and said graphite produces a % removal for said sheared DRA of about 35% or more at from about 8 to about 12 ppm DRA concentration and at about 1 g graphite/100 ml fuel.

8. The method of claim 5 wherein said DRA comprises unsheared DRA and said graphite produces a % DRA removal for said unsheared DRA of about 40% or more at about 1 g graphite/100 ml fuel.

9. The method of claim 5 wherein said DRA comprises unsheared DRA and said graphite produces a % DRA removal for said unsheared DRA of about 50% or more at from about 8 to about 12 ppm DRA concentration and at about 1 g graphite/100 ml fuel.

10. The method of claim 1 wherein the liquid hydrocarbon fuel has a boiling range of from about 150° F. to about 750° F.

11. The method of claim 1 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

12. The method of claim 1 wherein the liquid hydrocarbon fuel is selected from the group consisting of diesel fuel, jet fuel, aviation gasoline, and motor gasoline.

13. The method of claim 1 wherein the liquid hydrocarbon fuel is jet fuel.

14. The method of claim 2 wherein the liquid hydrocarbon fuel has a boiling range of from about 150° F. to about 750° F.

15. The method of claim 2 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

16. The method of claim 2 wherein the liquid hydrocarbon fuel is selected from the group consisting of diesel fuel, jet fuel, aviation gasoline, and motor gasoline.

17. The method of claim 2 wherein the liquid hydrocarbon fuel is jet fuel.

18. The method of claim 6 wherein the liquid hydrocarbon fuel has a boiling range of from about 150° F. to about 750° F.

19. The method of claim 6 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

20. The method of claim 6 wherein the liquid hydrocarbon fuel is selected from the group consisting of diesel fuel, jet fuel, aviation gasoline, and motor gasoline.

21. The method of claim 6 wherein the liquid hydrocarbon fuel is jet fuel.

22. The method of claim 8 wherein the liquid hydrocarbon fuel has a boiling range of from about 150° F. to about 750° F.

23. The method of claim 8 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

24. The method of claim 8 wherein the liquid hydrocarbon fuel is selected from the group consisting of diesel fuel, jet fuel, aviation gasoline, and motor gasoline.

25. The method of claim 8 wherein the liquid hydrocarbon fuel is jet fuel.

26. The method of claim 4 wherein the liquid hydrocarbon fuel has a boiling range of from about 150° F. to about 750° F.

27. The method of claim 4 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

28. The method of claim 4 wherein the liquid hydrocarbon fuel is selected from the group consisting of diesel fuel, jet fuel, aviation gasoline, and motor gasoline.

29. The method of claim 4 wherein the liquid hydrocarbon fuel is jet fuel.

30. The method of claim 5 wherein the liquid hydrocarbon fuel has a boiling range of from about 150° F. to about 750° F.

31. The method of claim 5 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

32. The method of claim 5 wherein the liquid hydrocarbon fuel is selected from the group consisting of diesel fuel, jet fuel, aviation gasoline, and motor gasoline.

33. The method of claim 5 wherein the liquid hydrocarbon fuel is jet fuel.

34. A method of removing drag reducer additive from liquid hydrocarbon fuel, said method comprising:
providing contaminated liquid hydrocarbon fuel comprising a concentration of drag reducer additive (DRA);
contacting said contaminated liquid hydrocarbon fuel with a quantity of one or more activated carbon effective to having an adsorption capacity for DRA of about 0.014% or more at from about 8 to about 12 ppm DRA concentration and at about 1 g activated carbon/100 ml fuel, said DRA being selected from the group consisting of sheared DRA, partially sheared DRA, and unsheared DRA, said contacting occurring under conditions effective to produce a clean liquid hydrocarbon fuel.

35. The method of claim 34 wherein said activated carbon has an adsorption capacity for said sheared DRA of 0.018% or more.

36. The method of claim 34 wherein said activated carbon has an adsorption capacity for said DRA of about 0.020% or more.

37. The method of claim 34 wherein said activated carbon has an adsorption capacity for said DRA of 0.025%.

38. The method of claim 34 wherein said activated carbon has an adsorption capacity for said DRA of about 0.030%.

39. The method of claim 34 wherein said activated carbon comprises activated carbon powder.

40. The method of claim 34 wherein said activated carbon comprises particulate having an average diameter of from about 1 micron to about 100 microns.

41. The method of claim 34 wherein said activated carbon produces a % removal for said DRA of about 20% or more at from about 8 to about 12 ppm DRA concentration and at about 1 g activated carbon/100 ml fuel.

42. The method of claim 34 wherein said activated carbon produces a % removal for unsheared DRA of about 30% or more at from about 8 to about 12 ppm DRA concentration and at about 1 g activated carbon/100 ml fuel.

43. The method of claim 34 wherein said activated carbon produces a % removal for unsheared DRA of about 40% or more at from about 8 to about 12 ppm DRA concentration and at about 1 g activated carbon/100 ml fuel.

44. The method of claim 34 wherein the liquid hydrocarbon fuel has a boiling range of from about 150° F. to about 750° F.

45. The method of claim 34 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

46. The method of claim 34 wherein the liquid hydrocarbon fuel is selected from the group consisting of diesel fuel, jet fuel, aviation gasoline, and motor gasoline.

47. The method of claim 34 wherein the liquid hydrocarbon fuel is jet fuel.

48. The method of claim 36 wherein the liquid hydrocarbon fuel has a boiling range of from about 150° F. to about 750° F.

49. The method of claim 36 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

50. The method of claim 36 wherein the liquid hydrocarbon fuel is selected from the group consisting of diesel fuel, jet fuel, aviation gasoline, and motor gasoline.

51. The method of claim 36 wherein the liquid hydrocarbon fuel is jet fuel.

52. The method of claim 38 wherein the liquid hydrocarbon fuel has a boiling range of from about 150° F. to about 750° F.

53. The method of claim 38 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

54. The method of claim 38 wherein the liquid hydrocarbon fuel is selected from the group consisting of diesel fuel, jet fuel, aviation gasoline, and motor gasoline.

55. The method of claim 38 wherein the liquid hydrocarbon fuel is jet fuel.

56. The method of claim 41 wherein the liquid hydrocarbon fuel has a boiling range of from about 150° F. to about 750° F.

57. The method of claim 41 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

58. The method of claim 41 wherein the liquid hydrocarbon fuel is selected from the group consisting of diesel fuel, jet fuel, aviation gasoline, and motor gasoline.

59. The method of claim 41 wherein the liquid hydrocarbon fuel is jet fuel.

60. The method of claim 42 wherein the liquid hydrocarbon fuel has a boiling range of from about 150° F. to about 750° F.

61. The method of claim 42 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

62. The method of claim 42 wherein the liquid hydrocarbon fuel is selected from the group consisting of diesel fuel, jet fuel, aviation gasoline, and motor gasoline.

63. The method of claim 42 wherein the liquid hydrocarbon fuel is jet fuel.

64. The method of claim 44 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

65. The method of claim 44 wherein the liquid hydrocarbon fuel is selected from the group consisting of diesel fuel, jet fuel, aviation gasoline, and motor gasoline.

66. The method of claim 44 wherein the liquid hydrocarbon fuel is jet fuel.

67. The method of claim 34 wherein said conditions comprise adding said quantity of said one or more effective activated carbons to said contaminated liquid hydrocarbon fuel in increments with agitation.

68. A method for selecting a drag reducer additive for a liquid hydrocarbon fuel comprising:
providing one or more samples of liquid hydrocarbon fuel comprising a single candidate DRA; and,
determining whether said single candidate DRA is removed from said liquid hydrocarbon fuel by a removal agent selected from the group consisting of a graphite and an activated carbon having an adsorption capacity for DRA of about 0.014% or more at from about 8 to about 12 ppm DRA concentration and at about 1 g removal agent/100 ml fuel; and,
selecting as said DRA only candidates which are removed from said liquid hydrocarbon fuel by said removal agent.

69. The method of claim 68 wherein said liquid hydrocarbon fuel in said samples is jet fuel.

70. A method of removing drag reducer additive from liquid hydrocarbon fuel, said method comprising:
providing contaminated liquid hydrocarbon fuel comprising a concentration of drag reducer additive (DRA), said DRA comprising polyalphaolefin produced by solution polymerization;
contacting said contaminated liquid hydrocarbon fuel with a quantity of removal agent under conditions effective to produce clean liquid hydrocarbon fuel, said removal agent being selected from the group consisting of one or more graphite and one or more activated carbon having an adsorption capacity for said DRA of about 0.014% or more at from about 8 to about 12 ppm DRA concentration and at about 1 g removal agent/100 ml fuel.

71. The method of claim 70 wherein said removal agent comprises graphite and said graphite comprises an adsorption capacity for DRA of about 0.02 wt. % or more at from about 8 to about 12 ppm DRA concentration and at about 1 g graphite/100 ml fuel, said DRA being selected from the group consisting of sheared DRA, partially sheared DRA, and unsheared DRA.

72. The method of claim 70 wherein said removal agent comprises graphite, said DRA comprises unsheared DRA, and said graphite comprises an adsorption capacity for said unsheared DRA of about 0.04 wt. % or more at from about 8 to about 12 ppm DRA concentration and at about 1 g graphite/100 ml fuel.

73. The method of claim 70 wherein said removal agent comprises graphite and said graphite produces a % polymer removal for unsheared DRA of about 25% or more at from about 8 to about 12 ppm DRA concentration and at about 1 g graphite/100 ml fuel.

74. The method of claim 70 wherein said removal agent comprises graphite and said graphite produces a % polymer removal for DRA of about 30% or more at from about 8 to about 12 ppm DRA concentration and at about 1 g graphite/100 ml fuel, said DRA being selected from the group consisting of sheared DRA, partially sheared DRA, and unsheared DRA.

75. The method of claim 70 wherein said removal agent comprises graphite and said graphite produces a % DRA removal for unsheared DRA of about 40% or more at about 1 g graphite/100 ml fuel.

76. The method of claim 70 wherein said removal agent comprises graphite, said DRA comprises unsheared DRA, and said graphite produces a % DRA removal for said unsheared DRA of about 50% or more at from about 8 to about 12 ppm DRA concentration and at about 1 g graphite/100 ml fuel.

77. The method of claim 70 wherein the liquid hydrocarbon fuel has a boiling range of from about 150° F. to about 750° F.

78. The method of claim 70 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

79. The method of claim 70 wherein the liquid hydrocarbon fuel is selected from the group consisting of diesel fuel, jet fuel, aviation gasoline, and motor gasoline.

80. The method of claim 70 wherein the liquid hydrocarbon fuel is jet fuel.

81. The method of claim 71 wherein the liquid hydrocarbon fuel has a boiling range of from about 150° F. to about 750° F.

82. The method of claim 71 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

83. The method of claim 71 wherein the liquid hydrocarbon fuel is selected from the group consisting of diesel fuel, jet fuel, aviation gasoline, and motor gasoline.

84. The method of claim 71 wherein the liquid hydrocarbon fuel is jet fuel.

85. The method of claim 72 wherein the liquid hydrocarbon fuel has a boiling range of from about 150° F. to about 750° F.

86. The method of claim 72 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

87. The method of claim 72 wherein the liquid hydrocarbon fuel is selected from the group consisting of diesel fuel, jet fuel, aviation gasoline, and motor gasoline.

88. The method of claim 72 wherein the liquid hydrocarbon fuel is jet fuel.

89. The method of claim 74 wherein the liquid hydrocarbon fuel has a boiling range of from about 150° F. to about 750° F.

90. The method of claim 74 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

91. The method of claim 74 wherein the liquid hydrocarbon fuel is selected from the group consisting of diesel fuel, jet fuel, aviation gasoline, and motor gasoline.

92. The method of claim 74 wherein the liquid hydrocarbon fuel is jet fuel.

93. The method of claim 3 wherein the liquid hydrocarbon fuel has a boiling range of from about 150° F. to about 750° F.

94. The method of claim 3 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

95. The method of claim 3 wherein the liquid hydrocarbon fuel is selected from the group consisting of diesel fuel, jet fuel, aviation gasoline, and motor gasoline.

96. The method of claim 3 wherein the liquid hydrocarbon fuel is jet fuel.

97. The method of claim 7 wherein the liquid hydrocarbon fuel has a boiling range of from about 150° F. to about 750° F.

98. The method of claim 7 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

99. The method of claim 7 wherein the liquid hydrocarbon fuel is selected from the group consisting of diesel fuel, jet fuel, aviation gasoline, and motor gasoline.

100. The method of claim 7 wherein the liquid hydrocarbon fuel is jet fuel.

101. The method of claim 9 wherein the liquid hydrocarbon fuel has a boiling range of from about 150° F. to about 750° F.

102. The method of claim 9 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

103. The method of claim 9 wherein the liquid hydrocarbon fuel is selected from the group consisting of diesel fuel, jet fuel, aviation gasoline, and motor gasoline.

104. The method of claim 9 wherein the liquid hydrocarbon fuel is jet fuel.

105. A method of removing drag reducer additive from a liquid hydrocarbon fuel, said method comprising:
  providing a contaminated liquid hydrocarbon fuel comprising a concentration of a drag reducer additive (DRA) comprising polymerized linear alpha olefin (LAO) monomers having from about 2 to about 40 carbon atoms;
  contacting said contaminated liquid hydrocarbon fuel with a quantity of a removal agent under conditions effective to produce a clean liquid hydrocarbon fuel, said removable agent being selected from the group consisting of one or more graphite and one or more activated carbon having an adsorption capacity for said DRA of about 0.014% or more at from about 8 to about 12 ppm DRA concentration and at about 1 g removal agent/100 ml fuel.

106. The method of claim 105 wherein said LAO monomers have from about 2 to about 30 carbon atoms.

107. The method of claim 105 wherein said LAO monomers have from about 4 to about 20 carbon atoms.

108. The method of claim 105 wherein said LAO monomers have from about 6 to about 12 carbon atoms.

109. The method of claim 105 wherein said removal agent comprises graphite and said graphite comprises an adsorption capacity for DRA of about 0.02 wt. % or more at from about 8 to about 12 ppm DRA concentration and at about 1 g graphite/100 ml fuel, said DRA being selected from the group consisting of sheared DRA, partially sheared DRA, and unsheared DRA.

110. The method of claim 105 wherein said removal agent comprises graphite, said DRA comprises unsheared DRA, and said graphite comprises an adsorption capacity for said unsheared DRA of about 0.04 wt. % or more at from about 8 to about 12 ppm DRA concentration and at about 1 g graphite/100 ml fuel.

111. The method of claim 105 wherein said removal agent comprises graphite, said DRA comprises unsheared DRA, and said graphite produces a % polymer removal for said unsheared DRA of about 25% or more at from about 8 to about 12 ppm DRA concentration and at about 1 g graphite/100 ml fuel.

112. The method of claim 105 wherein said removal agent comprises graphite and said graphite produces a % polymer removal for DRA of about 30% or more at from about 8 to about 12 ppm DRA concentration and at about 1 g graphite/100 ml fuel, said DRA being selected from the group consisting of sheared DRA, partially sheared DRA, and unsheared DRA.

113. The method of claim 105 wherein said removal agent comprises graphite, said DRA comprises unsheared DRA, and said graphite produces a % DRA removal for said unsheared DRA of about 40% or more at about 1 g graphite/100 ml fuel.

114. The method of claim 105 wherein said removal agent comprises graphite, said DRA comprises unsheared DRA, and said graphite produces a % DRA removal for said unsheared DRA of about 50% or more at from about 8 to about 12 ppm DRA concentration and at about 1 g graphite/100 ml fuel.

115. The method of claim 108 wherein said removal agent comprises graphite and said graphite comprises an adsorption capacity for DRA of about 0.02 wt. % or more at from about 8 to about 12 ppm DRA concentration and at about 1 g graphite/100 ml fuel, said DRA being selected from the group consisting of sheared DRA, partially sheared DRA, and unsheared DRA.

116. The method of claim 108 wherein said removal agent comprises graphite and said graphite produces a % polymer removal for DRA of about 30% or more at from about 8 to about 12 ppm DRA concentration and at about 1 g graphite/100 ml fuel, said DRA being selected from the group consisting of sheared DRA, partially sheared DRA, unsheared DRA.

117. The method of claim 108 wherein the liquid hydrocarbon fuel has a boiling range of from about 150° F. to about 750° F.

118. The method of claim 105 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

119. The method of claim 105 wherein the liquid hydrocarbon fuel is selected from the group consisting of diesel fuel, jet fuel, aviation gasoline, and motor gasoline.

120. The method of claim 105 wherein the liquid hydrocarbon fuel is jet fuel.

121. A method of removing drag reducer additive from liquid hydrocarbon fuel, said method comprising:
providing contaminated liquid hydrocarbon fuel comprising a concentration of drag reducer additive (DRA) comprising polymerized linear alpha olefin (LAO) monomers having from about 6 to about 12 carbon atoms, wherein said LAO monomers comprise two different LAO's which differ in number of carbon atoms by 6;
contacting said contaminated liquid hydrocarbon fuel with a quantity of removal agent under conditions effective to produce clean liquid hydrocarbon fuel, said removal agent being selected from the group consisting of one or more graphite and one or more activated carbon having an adsorption capacity for said DRA of about 0.014% or more at from about 8 to about 12 ppm DRA concentration and at about 1 g removal agent/100 ml fuel.

122. The method of claim 121 wherein said removal agent comprises graphite and said graphite comprises an adsorption capacity for DRA of about 0.02 wt. % or more at from about 8 to about 12 ppm DRA concentration and at about 1 g graphite/100 ml fuel, said DRA being selected from the group consisting of sheared DRA, partially sheared DRA, and unsheared DRA.

123. The method of claim 121 wherein said removal agent comprises graphite, said DRA comprises unsheared DRA, and said graphite comprises an adsorption capacity for said unsheared DRA of about 0.04 wt. % or more at from about 8 to about 12 ppm DRA concentration and at about 1 g graphite/100 ml fuel.

124. The method of claim 121 wherein said removal agent comprises graphite, said DRA comprises unsheared DRA, and said graphite produces a % polymer removal for unsheared DRA of about 25% or more at from about 8 to about 12 ppm DRA concentration and at about 1 g graphite/100 ml fuel.

125. The method of claim 121 wherein said removal agent comprises graphite and said graphite produces a % polymer removal for DRA of about 30% or more at from about 8 to about 12 ppm DRA concentration and at about 1 g graphite/100 ml fuel, said DRA being selected from the group consisting of sheared DRA, partially sheared DRA, and unsheared DRA.

126. The method of claim 121 wherein said removal agent comprises graphite, said DRA comprises unsheared DRA, and said graphite produces a % DRA removal for said unsheared DRA of about 40% or more at about 1 g graphite/100 ml fuel.

127. The method of claim 121 wherein said removal agent comprises graphite, said DRA comprises unsheared DRA, and said graphite produces a % DRA removal for said unsheared DRA of about 50% or more at from about 8 to about 12 ppm DRA concentration and at about 1 g graphite/100 ml fuel.

128. The method of claim 121 wherein the liquid hydrocarbon fuel has a boiling range of from about 150° F. to about 750° F.

129. The method of claim 121 wherein said liquid hydrocarbon fuel is selected from the group consisting of liquefied natural gas (LNG), liquefied petroleum gas (LPG), distillate fuels, No. 2 oil, residual fuel, No. 6 fuel, and bunker fuel.

130. The method of claim 121 wherein the liquid hydrocarbon fuel is selected from the group consisting of diesel fuel, jet fuel, aviation gasoline, and motor gasoline.

131. The method of claim 121 wherein the liquid hydrocarbon fuel is jet fuel.

132. The method of claim 122 wherein the liquid hydrocarbon fuel has a boiling range of from about 150° F. to about 750° F.

133. The method of claim 122 wherein the liquid hydrocarbon fuel is selected from the group consisting of diesel fuel, jet fuel, aviation gasoline, and motor gasoline.

134. The method of claim 122 wherein the liquid hydrocarbon fuel is jet fuel.

135. The method of claim 125 wherein the liquid hydrocarbon fuel has a boiling range of from about 150° F. to about 750° F.

136. The method of claim 125 wherein the liquid hydrocarbon fuel is selected from the group consisting of diesel fuel, jet fuel, aviation gasoline, and motor gasoline.

137. The method of claim 125 wherein the liquid hydrocarbon fuel is jet fuel.

* * * * *